United States Patent
Yaacobi

(10) Patent No.: US 6,669,950 B2
(45) Date of Patent: *Dec. 30, 2003

(54) OPHTHALMIC DRUG DELIVERY DEVICE

(75) Inventor: Yoseph Yaacobi, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/187,006

(22) Filed: Jul. 1, 2002

(65) Prior Publication Data

US 2003/0003129 A1 Jan. 2, 2003

Related U.S. Application Data

(63) Continuation of application No. 09/664,790, filed on Sep. 19, 2000, now Pat. No. 6,416,777.
(60) Provisional application No. 60/160,673, filed on Oct. 21, 1999.

(51) Int. Cl.[7] .............................. A61F 2/14; A61F 2/00
(52) U.S. Cl. ...................... 424/428; 424/427; 424/423; 424/422
(58) Field of Search .................. 424/428, 427, 424/423, 422

(56) References Cited

U.S. PATENT DOCUMENTS

| 3,416,530 A | 12/1968 | Ness |
| 3,828,777 A | 8/1974 | Ness |
| 4,014,335 A | 3/1977 | Arnold |

(List continued on next page.)

FOREIGN PATENT DOCUMENTS

| DE | 40 22 553 | 1/1992 |
| EP | 0 904 787 | 3/1999 |
| RU | 2149615 | 5/2000 |

(List continued on next page.)

OTHER PUBLICATIONS

"Bausch & Lomb and Control Delivery Systems Agree to Develop Breakthrough Therapeutic Products for Severe Eye Diseases;" Business Wire via First!; NewsEdge Corp.; Jun. 15, 1999; 4 pp.

"Method of Placing Irrigation System into Tenon's Space," E.I. Sidorenko, et al., Abstract of Russian Patent No. RU 2123314, issued Dec. 20, 1998, 1 pg.

"A New method for Posterior Sub–Tenon's Drug Adimistration," Nesterov, et al., Ophthalmic Surgery, vol. 24, No. 1, Jan. 1993, pp. 59–61.

Dialog File 266:FEDRIP database record; Identifying No. 122098; "Implantation of a Sub–Tenon Drug Delivery Device Loaded with a Test Article in Rabbits and Distribution of the Test Article in Ocular Tissues;" Compiled and distributed by NTIS; 1 page; Jun. 03, 1999.

Dialog File 266: FEDRIP database record: Identifying No. 134284; "Implantation of a Sub–Tenon Drug Delivery Device Loaded with a Test Article in Rabbits and Distribution of the Test Article in Ocular Tissues," Compiled and distributed by NTIS; 1 page No Date Available.

Dialog File 266: FEDRIP database record; Identifiying No. 131476; Ocular Bioavailability of AL–3789 and AL–4940 after Sub–Tenon's Injection of AL 3789 Ophthalmic Suspensions in New Zealand White Rabbits; Compiled and distributed by NTIS; 1 page No Date Available.

Primary Examiner—Thurman K. Page
Assistant Examiner—Rachel M. Bennett
(74) Attorney, Agent, or Firm—W. David Lee

(57) ABSTRACT

The present invention is directed to a drug delivery device for a human eye. The human eye has a sclera, an inferior oblique muscle, and a macula. The device of the present invention includes a pharmaceutically active agent, and a geometry that facilitates the implantation of the device on an outer surface of the sclera, beneath the inferior oblique muscle, and with the pharmaceutically active agent disposed above the macula. Methods of delivery a pharmaceutically active agent to the posterior segment of the human eye are also disclosed.

12 Claims, 12 Drawing Sheets

U.S. PATENT DOCUMENTS

| | | |
|---|---|---|
| 4,300,557 A | 11/1981 | Refojo et al. |
| 4,327,725 A | 5/1982 | Cortese et al. |
| 4,853,224 A | 8/1989 | Wong |
| 4,946,450 A | 8/1990 | Erwin |
| 4,997,652 A | 3/1991 | Wong |
| 5,147,647 A | 9/1992 | Darougar |
| 5,164,188 A | 11/1992 | Wong |
| 5,178,635 A | 1/1993 | Gwon et al. |
| 5,300,114 A | 4/1994 | Gwon et al. |
| 5,322,691 A | 6/1994 | Darougar et al. |
| 5,378,475 A | 1/1995 | Smith et al. |
| 5,403,901 A | 4/1995 | Namdaran et al. |
| 5,443,505 A | 8/1995 | Wong et al. |
| 5,466,466 A | 11/1995 | Muller |
| 5,476,511 A | 12/1995 | Gwon et al. |
| 5,516,522 A | 5/1996 | Peyman et al. |
| 5,632,984 A | 5/1997 | Wong et al. |
| 5,679,666 A | 10/1997 | Clark |
| 5,710,165 A | 1/1998 | Kapin et al. |
| 5,725,493 A | 3/1998 | Avery et al. |
| 5,743,274 A | 4/1998 | Peyman |
| 5,766,242 A | 6/1998 | Wong et al. |
| 5,766,619 A | 6/1998 | Aiache et al. |
| 5,770,592 A | 6/1998 | Clark |
| 5,773,019 A | 6/1998 | Ashton et al. |
| 5,797,898 A | 8/1998 | Santini, Jr. et al. |
| 5,824,072 A | 10/1998 | Wong |
| 5,824,073 A | 10/1998 | Peyman |
| 5,830,173 A | 11/1998 | Avery et al. |
| 5,836,935 A | 11/1998 | Ashton et al. |
| 5,902,598 A | 5/1999 | Chen et al. |
| 5,904,144 A | 5/1999 | Hammang et al. |
| 5,916,584 A | 6/1999 | O'Donoghue et al. |
| 6,001,386 A | 12/1999 | Ashton et al. |
| 6,074,661 A | 6/2000 | Olejnik et al. |
| 6,110,485 A | 8/2000 | Olejnik |
| 6,126,687 A | 10/2000 | Peyman |
| 6,146,366 A | 11/2000 | Schachar |
| 6,217,895 B1 | 4/2001 | Guo et al. |
| 6,375,972 B1 | 4/2002 | Guo et al. |
| 6,416,777 B1 * | 7/2002 | Yaacobi ...................... 424/428 |

FOREIGN PATENT DOCUMENTS

| | | |
|---|---|---|
| WO | WO 94/05257 | 3/1994 |
| WO | WO 95/26734 | 10/1995 |
| WO | WO 95/28984 | 11/1995 |
| WO | WO 96/36377 | 11/1996 |
| WO | WO 97/14415 | 4/1997 |
| WO | WO 98/23228 | 6/1998 |
| WO | WO 98/43611 | 10/1998 |
| WO | WO 99/07418 | 2/1999 |
| WO | WO 99/11244 | 3/1999 |
| WO | WO 99/32104 | 7/1999 |
| WO | WO 99/45920 | 9/1999 |
| WO | WO 00/56340 | 3/2000 |
| WO | WO 00/37066 | 6/2000 |

* cited by examiner

OPHTHALMIC DRUG DELIVERY DEVICE

This application is a continuation of U.S. application Ser. No. 09/664,790, filed Sep. 19, 2000, now U.S. Pat. No. 6,416,777, which claims priority from U.S. Provisional Application No. 60/160,673, filed Oct. 21, 1999.

FIELD OF THE INVENTION

The present invention generally pertains to biocompatible implants for localized delivery of pharmaceutically active agents to body tissue. More particularly, but not by way of limitation, the present invention pertains to biocompatible implants for localized delivery of pharmaceutically active agents to the posterior segment of the eye.

DESCRIPTION OF THE RELATED ART

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, three main methods of treatment are currently being developed, (a) photocoagulation, (b) the use of angiogenesis inhibitors, and (c) photodynamic therapy. Photocoagulation is the most common treatment modality for CNV. However, photocoagulation can be harmful to the retina and is impractical when the CNV is near the fovea. Furthermore, over time, photocoagulation often results in recurrent CNV. Oral or parenteral (non-ocular) administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Periocular injections of these compounds often result in the drug being quickly washed out and depleted from the eye, via periocular vasculature and soft tissue, into the general circulation. Repetitive intraocular injections may result in severe, often blinding, complications such as retinal detachment and endophthalmitis. Photodynamic therapy is a new technology for which the long-term efficacy is still largely unknown.

In order to prevent complications related to the above-described treatments and to provide better ocular treatment, researchers have suggested various implants aimed at localizing delivery of anti-angiogenic compounds to the eye. U.S. Pat. No. 5,824,072 to Wong discloses a non-biodegradable polymeric implant with a pharmaceutically active agent disposed therein. The pharmaceutically active agent diffuses through the polymer body of the implant into the target tissue. The pharmaceutically active agent may include drugs for the treatment of macular degeneration and diabetic retinopathy. The implant is placed substantially within the tear fluid upon the outer surface of the eye over an avascular region, and may be anchored in the conjunctiva or sclera; episclerally or intrasclerally over an avascular region; substantially within the suprachoroidial space over an avascular region such as the pars plana or a surgically induced avascular region; or in direct communication with the vitreous.

U.S. Pat. No. 5,476,511 to Gwon et al. discloses a polymer implant for placement under the conjunctiva of the eye. The implant may be used to deliver neovascular inhibitors for the treatment of ARMD and drugs for the treatment of retinopathies, and retinitis. The pharmaceutically active agent diffuses through the polymer body of the implant.

U.S. Pat. No. 5,773,019 to Ashton et al. discloses a non-bioerodable polymer implant for delivery of certain drugs including angiostatic steroids and drugs such as cyclosporine for the treatment of uveitis. Once again, the pharmaceutically active agent diffuses through the polymer body of the implant.

All of the above-described implants require careful design and manufacture to permit controlled diffusion of the pharmaceutically active agent through a polymer body (i.e., matrix devices) or polymer membrane (i.e., reservoir devices) to the desired site of therapy. Drug release from these devices depends on the porosity and diffusion characteristics of the matrix or membrane, respectively. These parameters must be tailored for each drug moiety to be used with these devices. Consequently, these requirements generally increase the complexity and cost of such implants.

U.S. Pat. No. 5,824,073 to Peyman discloses an indentor for positioning in the eye. The indentor has a raised portion that is used to indent or apply pressure to the sclera over the macular area of the eye. This patent discloses that such pressure decreases choroidal congestion and blood flow through the subretinal neovascular membrane, which, in turn, decreases bleeding and subretinal fluid accumulation.

Therefore, a need exists in the biocompatible implant field for a surgically implantable ophthalmic drug delivery device capable of safe, effective, rate-controlled, localized delivery of a wide variety of pharmaceutically active agents. The surgical procedure for implanting such a device should be safe, simple, quick, and capable of being performed in an outpatient setting. Ideally, such a device should be easy and economical to manufacture. Furthermore, because of its versatility and capability to deliver a wide variety of pharmaceutically active agents, such an implant should be capable of use in ophthalmic clinical studies to deliver various agents that create a specific physical condition in a patient. Such an ophthalmic drug delivery device is especially needed for localized delivery of pharmaceutically active agents to the posterior segment of the eye to combat ARMD, CNV, retinopathies, retinitis, uveitis, macular edema, glaucoma, and neuropathies.

SUMMARY OF THE INVENTION

The present invention is directed to a drug delivery device for a human eye. The human eye has a sclera, an inferior oblique muscle, and a macula. The device of the present invention includes a pharmaceutically active agent, and a geometry that facilitates the implantation of the device on an outer surface of the sclera, beneath the inferior oblique muscle, and with the pharmaceutically active agent disposed above the macula. Because of its unique geometry, the device is especially useful for localized delivery of pharmaceutically active agents to the posterior segment of the eye to combat ARMD, CNV, retinopathies, retinitis, uveitis, macular edema, glaucoma, and neuropathies.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 21 of the drawings, like numerals being used for like and corresponding parts of the various drawings.

Figure 1:
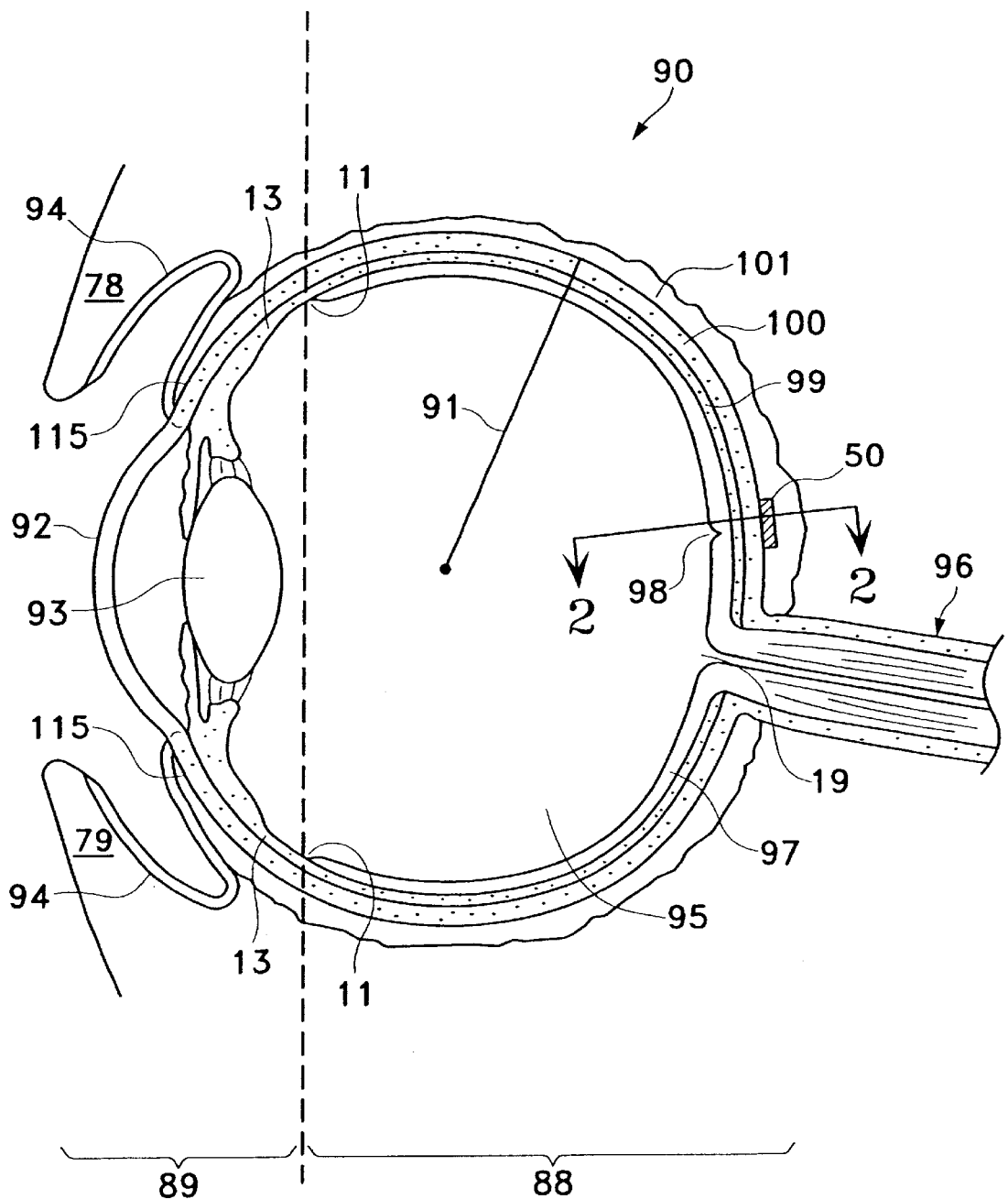
FIG. 1 is a side sectional view schematically illustrating the human eye and an ophthalmic drug delivery device implanted in the posterior segment of the eye according to the present invention.

FIGS. 1 through 6 illustrate various portions of the human eye important to a complete understanding of the present invention. Referring first to FIG. 1, a human eye 90 is schematically illustrated. Eye 90 has a cornea 92, a lens 93, vitreous 95, a sclera 100, a choroid 99, a retina 97, and an optic nerve 96. Eye 90 is generally divided into an anterior segment 89 and a posterior segment 88. Anterior segment 89 of eye 90 generally includes the portions of eye 90 anterior of ora serata 11. Posterior segment 88 of eye 90 generally includes the portions of eye 90 posterior of ora serata 11. Retina 97 is physically attached to choroid 99 in a circumferential manner proximate pars plana 13, posteriorly to optic disk 19. Retina 97 has a macula 98 located slightly lateral to optic disk 19. As is well known in the ophthalmic art, macula 98 is comprised primarily of retinal cones and is the region of maximum visual acuity in retina 97. A Tenon's capsule or Tenon's membrane 101 is disposed on sclera 100. A conjunctiva 94 covers a short area of the globe of eye 90 posterior to limbus 115 (the bulbar conjunctiva) and folds up (the upper cul-de-sac) or down (the lower cul-de-sac) to cover the inner areas of upper eyelid 78 and lower eyelid 79, respectively. Conjunctiva 94 is disposed on top of Tenon's capsule 101.

Figure 2:
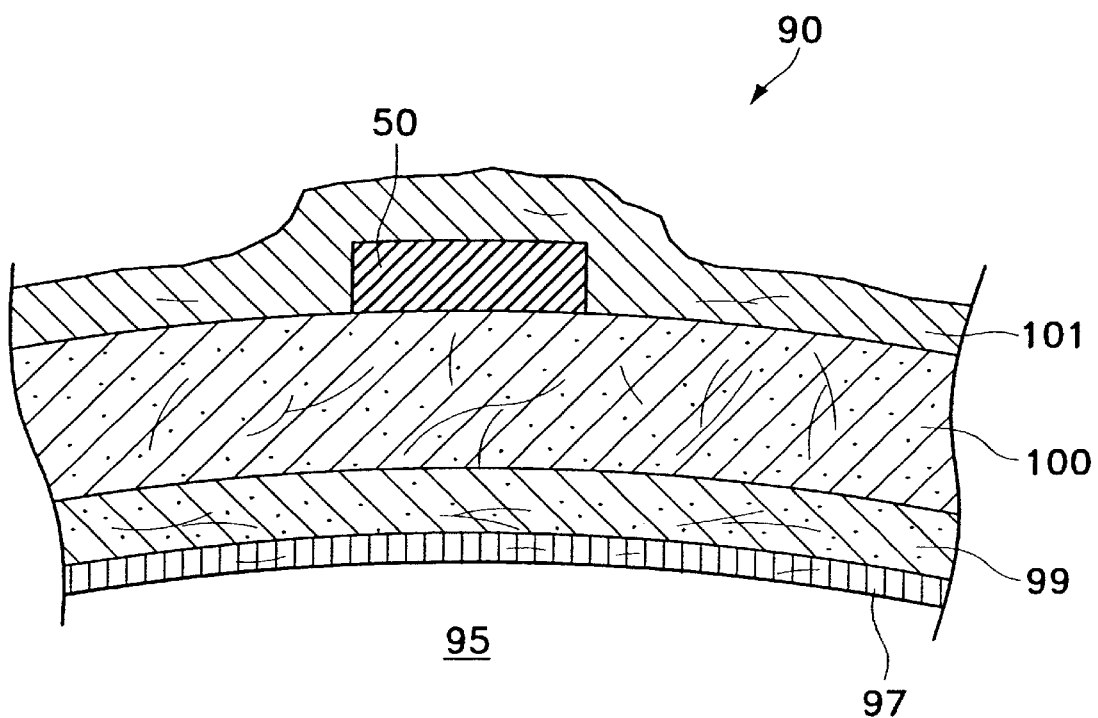
FIG. 2 is detailed cross-sectional view of the eye of FIG. 1 along line 2—2.

As is shown in FIGS. 1 and 2, and as is described in greater detail hereinbelow, device 50 is preferably disposed directly on the outer surface of sclera 100, below Tenon's capsule 101 for treatment of most posterior segment diseases or conditions. In addition, for treatment of ARMD and CNV in humans, device 50 is preferably disposed directly on the outer surface of sclera 100, below Tenon's capsule 101, with an inner core of device 50 proximate macula 98.

Figure 3:
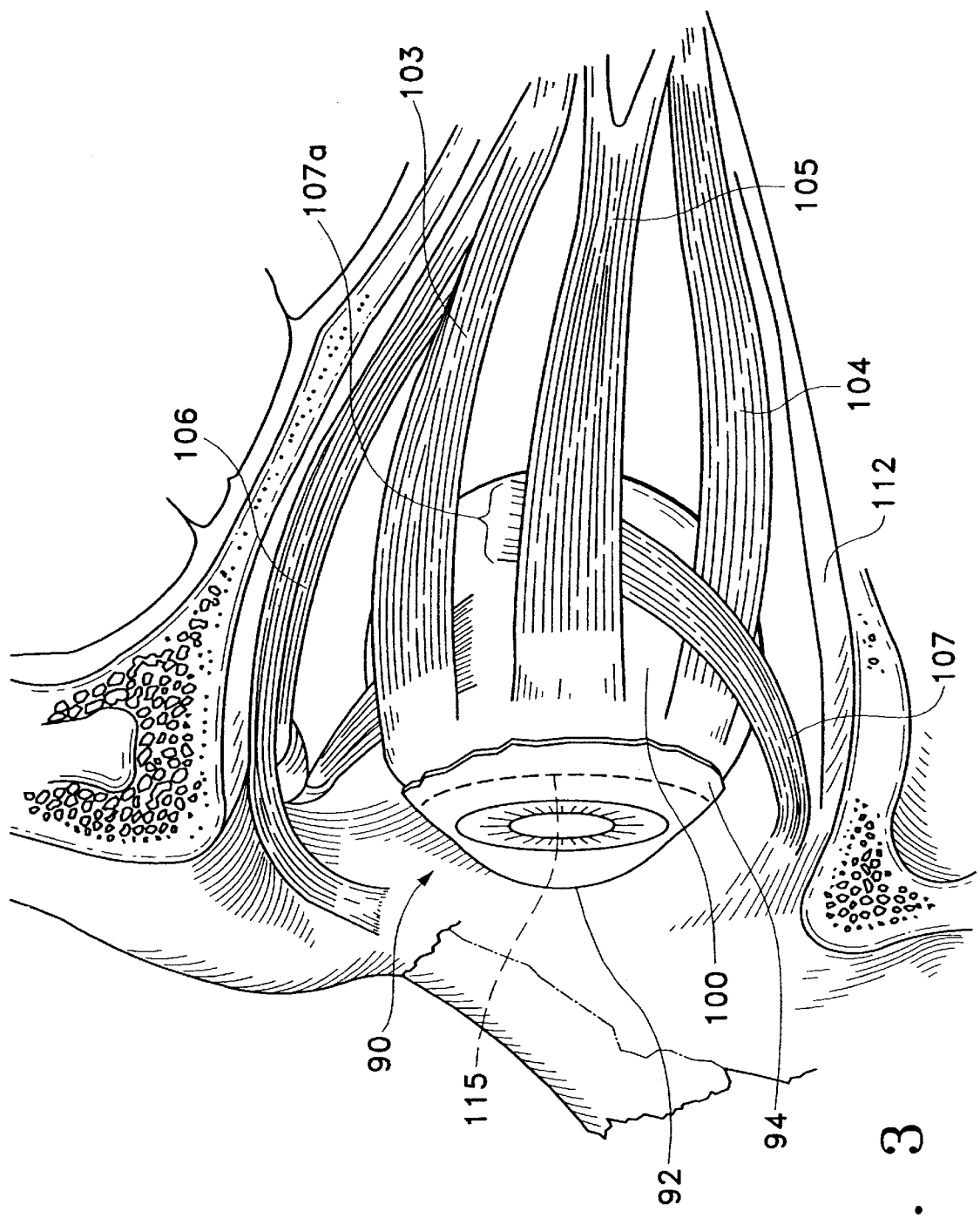
FIG. 3 is a three dimensional schematic representation of the human eye in situ.

FIG. 3 illustrates a left human eye 90 within its orbit 112. As can be seen from FIG. 3, inferior oblique muscle 107 runs under lateral rectus muscle 105. The insertion line 107a of inferior oblique muscle 107 into sclera 100 is located just above the superior border of lateral rectus muscle 105. Of course, the position of the inferior oblique muscle in a right human eye 90 is a mirror image to its position on left human eye 90 of FIG. 3. Cornea 92, conjunctiva 94, superior rectus muscle 103, inferior rectus muscle 104, superior oblique muscle 106, and limbus 115 are also shown in FIG. 3.

Figure 4:
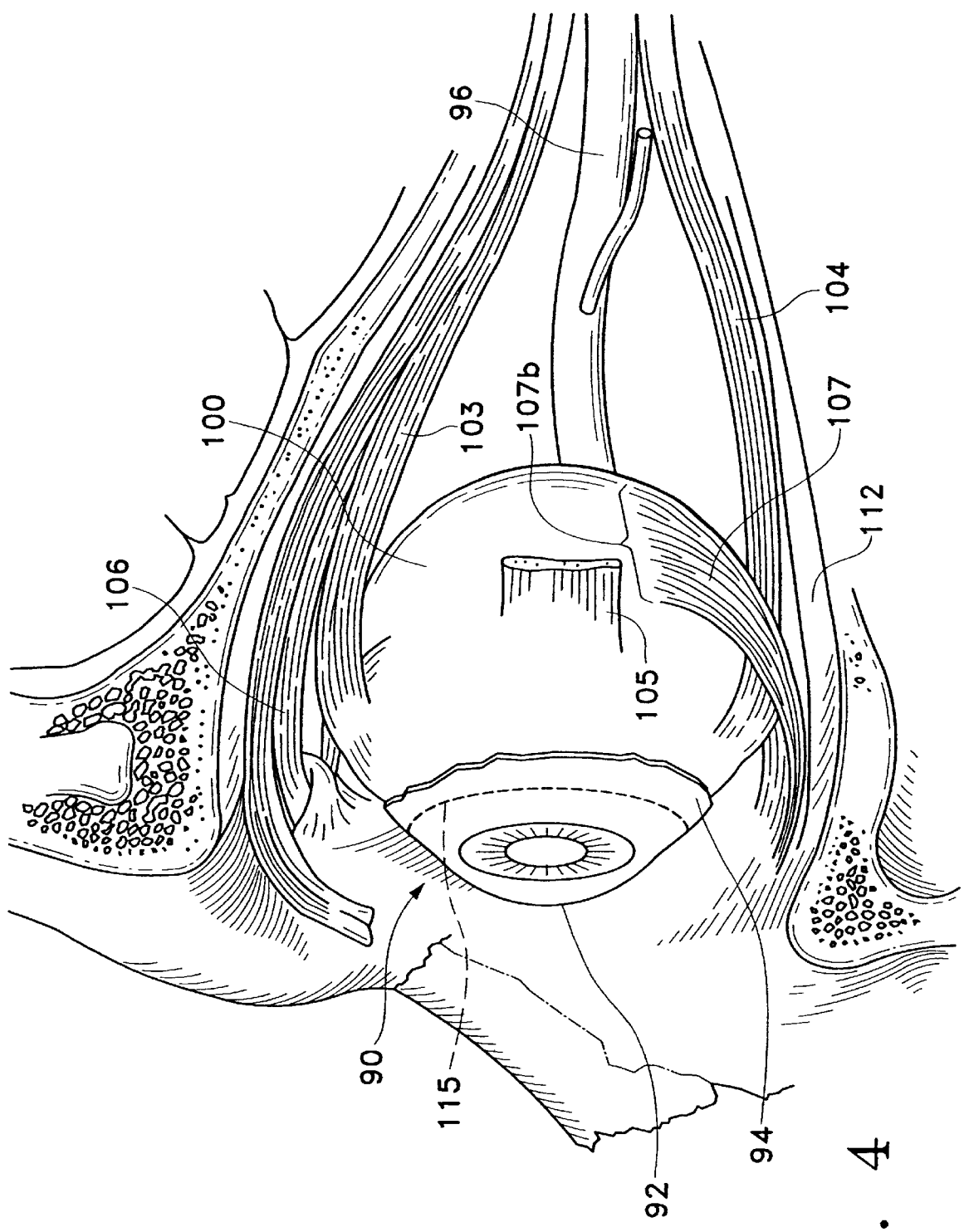
FIG. 4 shows the eye of FIG. 3 after partial removal of the lateral rectus muscle.

FIG. 4 similarly shows a left human eye 90 within its orbit 112. However, a portion of lateral rectus muscle 105 is not shown in FIG. 4 to allow visibility of the portion of sclera 100 and optic nerve 96 usually hidden by the muscle. In FIG. 4, an insertion line 107b of inferior oblique muscle 107 into sclera 100 is lower than insertion line 107a of FIG. 3, indicating the representative physiological variability of the insertion line of the inferior oblique muscle in the human eye.

Figure 5:
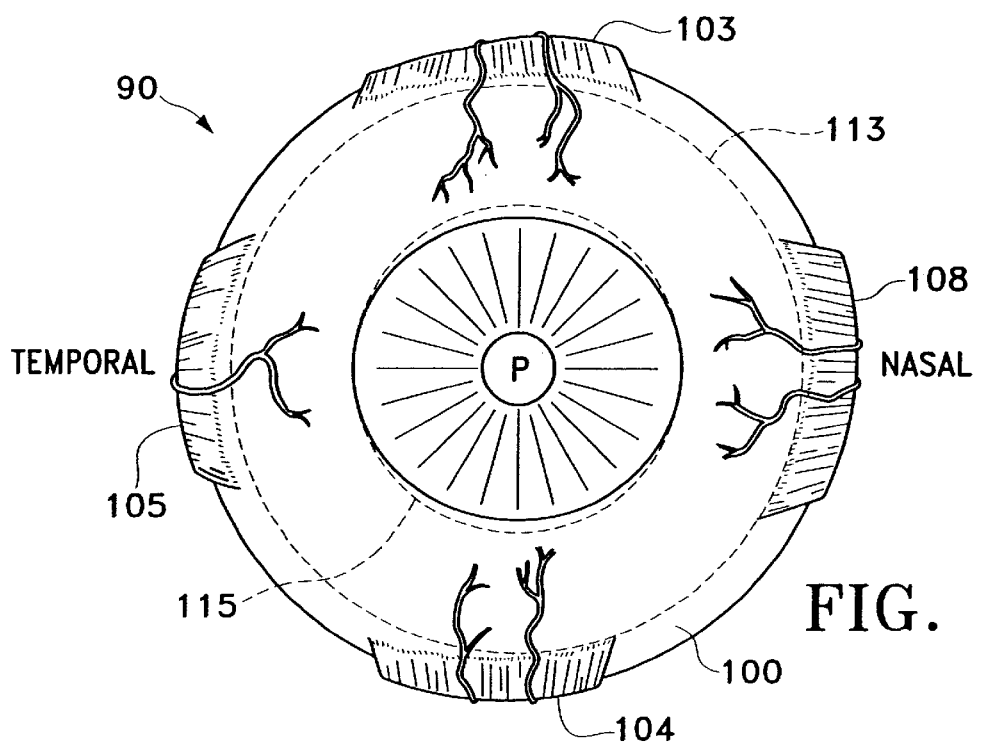
FIG. 5 is a schematic representation of the anterior view of a human eye.

FIG. 5 schematically illustrates an anterior view of human eye 90 with its four recti muscles, the superior rectus muscle 103, the medial rectus muscle 108, the inferior rectus muscle 104, and the lateral rectus muscle 105. FIG. 5 also shows the relationship between the limbus, represented in FIG. 5 by circumferential line 115, and the insertion lines of the recti muscles, represented in FIG. 5 by circumferential lines 113.

Figure 6:
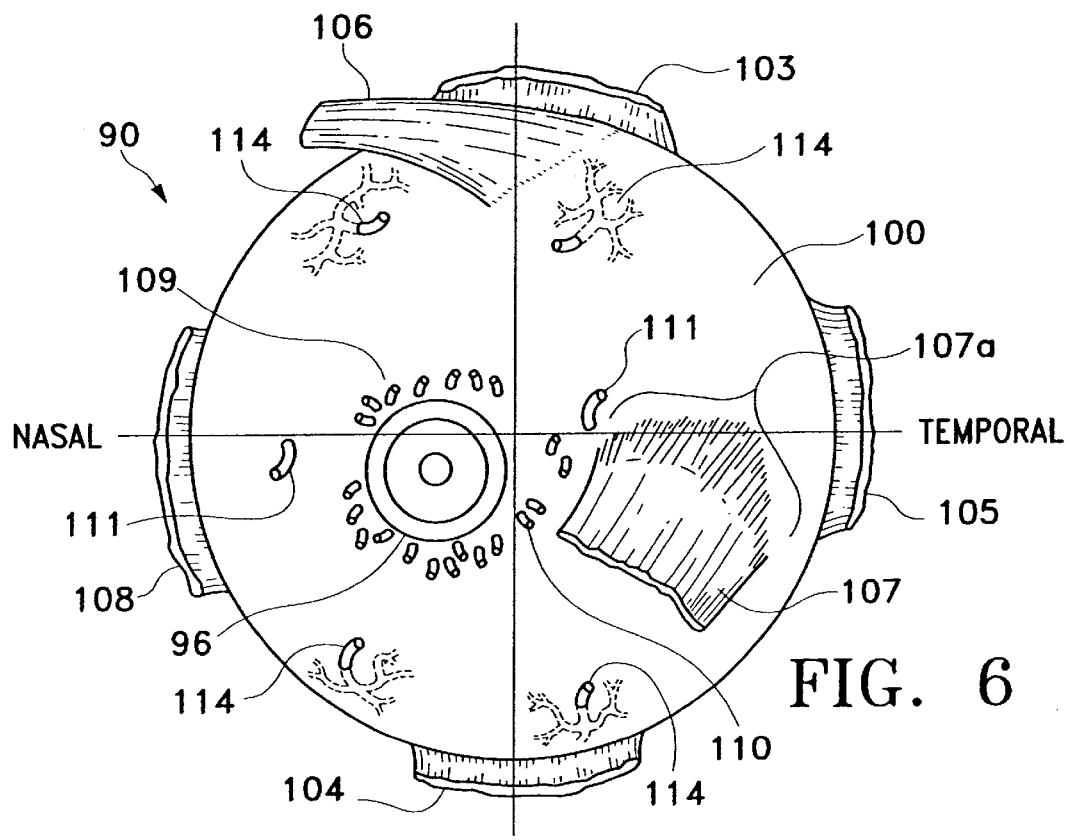
FIG. 6 is a schematic representation of the posterior view of a human eye.

The posterior view of human eye 90 is schematically illustrated in FIG. 6. FIG. 6 shows the locations of the superior rectus muscle 103, the lateral rectus muscle 105, the inferior rectus muscle 104, the medial rectus muscle 108, the superior oblique muscle 106, the inferior oblique muscle 107 and its insertion line 107a, the optic nerve 96, the cilliary vessels 109, the sclera 100, the scleral area 110 above macula 98, the long cilliary arteries 111, and the vortex veins 114.

Figure 7:
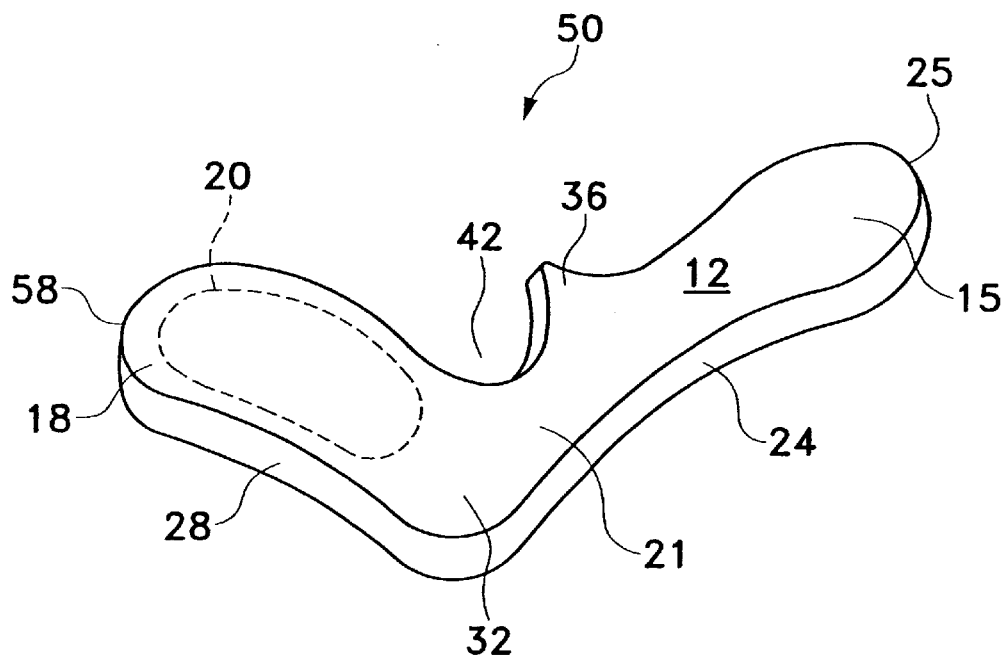
FIG. 7 is a perspective, orbital view of an ophthalmic drug delivery device for the right human eye according to a first preferred embodiment of the present invention.
Figure 9:
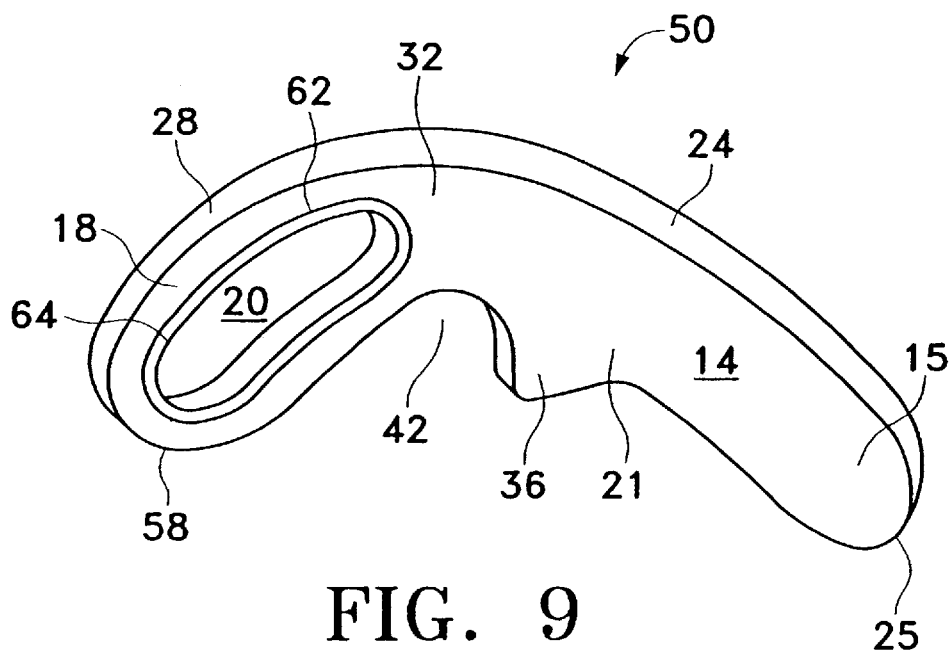
FIG. 9 is a perspective, scleral view of the ophthalmic drug delivery device of FIG. 7.

FIGS. 7 and 9 schematically illustrate an ophthalmic drug delivery device 50 for the right human eye according to a first preferred embodiment of the present invention. Device 50 may be used in any case where localized delivery of a pharmaceutically active agent to the eye is required. Device 50 is particularly useful for localized delivery of pharmaceutically active agents to the posterior segment of the eye. A preferred use for device 50 is the delivery of pharmaceutically active agents to the retina proximate the macula for treating ARMD, choroidial neovascularization (CNV), retinopathies, retinitis, uveitis, macular edema, glaucoma, and neuropathies.

Device 50 generally includes a body 21 having a convex, dome-shaped, orbital surface 12 and a concave, dome-shaped, scleral surface 14. Scleral surface 14 is designed with a radius of curvature that facilitates direct contact with sclera 100. Most preferably, scleral surface 14 is designed with a radius of curvature equal to the radius of curvature 91 of an average human eye 90. (See FIG. 1) Orbital surface 12 is preferably designed with a radius of curvature that facilitates implantation under Tenon's capsule 101. When viewed from the top, body 21 preferably has a generally "F-shaped" geometry with a longitudinal part 15, a transversal part 18, and a knee 32 therebetween. Longitudinal part 15 and transversal part 18 are preferably joined at knee 32 to form an angle of about ninety degrees. Longitudinal part 15 has a proximal end 25, a rounded edge 24, a stopper 36, and a notch 42. As is described in more detail hereinbelow, notch 42 is designed to accommodate the origin of inferior oblique muscle 107. Stopper 36 defines the lower portion of notch 42 and is preferably slightly elevated from the remainder of the generally convex orbital surface 12. As is described in greater detail hereinbelow, stopper 36 is designed to prevent excessive advancement of device 50 toward optic nerve 96 through contact on the anterior border of inferior oblique muscle 107. Transversal part 18 has a distal end 58, a rounded edge 28, and a well or cavity 20 having an opening 64 to scleral surface 14. Well 20 and opening 64 preferably have a generally oval shape. As is explained in more detail hereinbelow, transversal part 18 allows cavity 20 to be placed more directly over the area of sclera 100 overlying macula 98.

Figure 10:
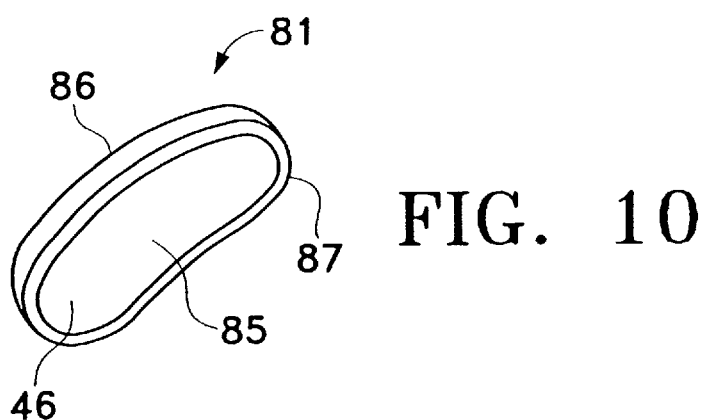
FIG. 10 is a perspective view of an oval shaped drug core or tablet for use with the ophthalmic drug delivery devices of the present invention.
Figure 11:
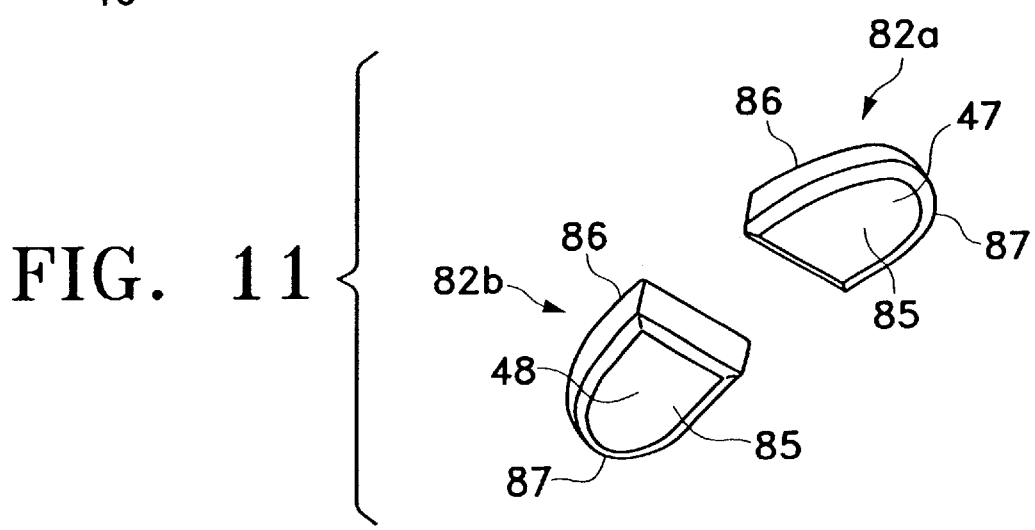
FIG. 11 is a perspective view of two, mating half-oval shaped drug cores or tablets for use with the ophthalmic drug delivery devices of the present invention.

An inner core 81, which is shown in FIG. 10, is preferably disposed in well 20. As shown in FIG. 10, inner core 81 is preferably a tablet comprising one or more pharmaceutically active agents. Tablet 81 preferably has a generally oval body 46 with a concave, dome-shaped, scleral surface 85 and a convex, dome-shaped, orbital surface 86. Body 46 also preferably has a peripheral bevel 87 disposed thereon. Alternatively, as shown in FIG. 11, the inner core may comprise mating, half-oval tablets 82a and 82b. Tablet 82a preferably has a body 47 identical to one half of body 46 of tablet 81. Tablet 82b preferably has a body 48 equal to the opposite half of body 46 of tablet 81. Still further in the alternative, inner core 81, or inner cores 82a and 82b, may comprise a conventional hydrogel, gel, paste, or other semi-solid dosage form having one or more pharmaceutically active agents disposed therein.

Returning to FIG. 9, a retaining member 62 is preferably disposed proximate opening 64. Retaining member 62 prevents inner core 81 from falling out of well 20. When inner core 81 is a tablet, retaining member 62 is preferably a continuous rim or lip disposed circumferentially around opening 64 that is designed to accommodate bevel 87 of tablet 81. Alternatively, retaining member 62 may comprise one or more members that extend from body 21 into opening 64.

Although not shown in FIGS. 9 through 11, inner core 81 may alternatively comprise a suspension, solution, powder, or combination thereof containing one or more pharmaceutically active agents. In this embodiment, scleral surface 14 is formed without opening 64, and the suspension, solution, powder, or combination thereof diffuses through a relatively thin extension of scleral surface 14 or other membrane below inner core 81. Still further in the alternative, device 50 may be formed without well 20 or inner core 81, and the pharmaceutically active agent(s) in the form of a suspension, solution, powder, or combination thereof may be dispersed throughout body 21 of device 50. In this embodiment, the pharmaceutically active agent diffuses through body 21 into the target tissue.

The geometry and dimensions of device 50 maximize communication between the pharmaceutically active agent of inner core 81 and the tissue underlying scleral surface 14. Scleral surface 14 preferably physically contacts the outer surface of sclera 100. Alternatively, scleral surface 14 may be disposed proximate the outer surface of sclera 100. By way of example, device 50 may be disposed in the periocular tissues just above the outer surface of sclera 100 or intralamellarly within sclera 100.

Body 21 preferably comprises a biocompatible, non-bioerodable material. Body 21 more preferably comprises a biocompatible, non-bioerodable polymeric composition. Said polymeric composition may be a homopolymer, a copolymer, straight, branched, cross-linked, or a blend. Examples of polymers suitable for use in said polymeric composition include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof. Examples of suitable soft acrylics are more fully disclosed in U.S. Pat. No. 5,403,901, which is incorporated herein in its entirety by reference. Said polymeric composition most preferably comprises silicone. Of course, said polymeric composition may also comprise other conventional materials that affect its physical properties, including, but not limited to, porosity, tortuosity, permeability, rigidity, hardness, and smoothness. Exemplary materials affecting certain ones of these physical properties include conventional plasticizers, fillers, and lubricants. Said polymeric composition may comprise other conventional materials that affect its chemical properties, including, but not limited to, toxicity, hydrophobicity, and body 21—inner core 81 interaction. Body 21 is preferably impermeable to the pharmaceutically active agent of inner core 81. When body 21 is made from a generally elastic polymeric composition, the shape of well 20 may be made slightly smaller than the shape of inner core 81. This frictional fit secures inner core 81 within well 20. In this embodiment, body 21 may be formed with or without retaining member 62, and inner core 81 may be formed with or without bevel 87, if desired.

Inner core 81 may comprise any ophthalmically acceptable pharmaceutically active agents suitable for localized delivery. Examples of pharmaceutically active agents suitable for inner core 81 are anti-infectives, including, without limitation, antibiotics, antivirals, and antifungals; antiallergenics and mast cell stabilizers; steroidal and non-steroidal anti-inflammatory agents; cyclooxygenase inhibitors, including, without limitation, Cox I and Cox II inhibitors; combinations of anti-infective and anti-inflammatory agents; anti-glaucoma agents, including, without limitation, adrenergics, β-adrenergic blocking agents, α-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of the posterior segment of the eye, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592, which are incorporated herein in their entirety by reference. Preferred ones of such angiostatic steroids include 4,9(11)-Pregnadien-17α, 21-diol-3,20-dione and 4,9(11)-Pregnadien-17α,21-diol-3, 20-dione-21-acetate. A preferred non-steroidal anti-inflammatory for the treatment of cystoid macular edema is nepafenac. Inner core 81 may also comprise conventional non-active excipients to enhance the stability, solubility, penetrability, or other properties of the active agent or the drug core.

If inner core 81 is a tablet, it may further comprise conventional excipients necessary for tableting, such as fillers and lubricants. Such tablets may be produced using conventional tableting methods. The pharmaceutically active agent is preferably distributed evenly throughout the tablet. In addition to conventional tablets, inner core 81 may comprise a special tablet that bioerodes at a controlled rate, releasing the pharmaceutically active agent. By way of example, such bioerosion may occur through hydrolosis or enzymatic cleavage. If inner core 81 is a hydrogel or other gel, such gels may bioerode at a controlled rate, releasing the pharmaceutically active agent. Alternatively, such gels may be non-bioerodable but allow diffusion of the pharmaceutically active agent.

Device 50 may be made by conventional polymer processing methods, including, but not limited to, injection molding, extrusion molding, transfer molding, and compression molding. Preferably, device 50 is formed using conventional injection molding techniques. Inner core 81 is preferably disposed in well 20 after the formation of body 21 of device 50. Retaining member 62 is preferably resilient enough to allow bevel 87 of inner core 81 to be inserted through opening 64 and then to return to its original position.

Device 50 is preferably surgically placed directly on the outer surface of sclera 100 below Tenon's capsule 101 with well 20 and inner core 81 directly over the area of sclera 100 above macula 98 using the following preferred technique that is capable of being performed in an outpatient setting. The surgeon first performs an 8 mm peritomy in one of the quadrants of eye 90. Preferably, the surgeon performs the peritomy in the infra-temporal quadrant, about 3 mm posterior to limbus 115 of eye 90. Once this incision is made, the surgeon performs a blunt dissection to separate Tenon's capsule 101 from sclera 100. Using scissors and blunt dissection, an antero-posterior tunnel is formed along the outer surface of sclera 100 and below inferior oblique muscle 107, preferably following the inferior border of lateral rectus muscle 105. The inferior oblique muscle 107 is then engaged with a Jamison muscle hook. The tip of the hook is then advanced just posterior to the inferior oblique muscle to form a portion of the tunnel that will accommodate transversal part 18 of device 50. Once the tunnel is formed, the surgeon uses Nuggett forceps to hold transversal part 18 of device 50 with scleral surface 14 facing sclera 100 and distal end 58 of transversal part 18 away from the surgeon. The surgeon then introduces device 50, distal end 58 first, into the tunnel at the level of the peritomy. Once in the tunnel, the surgeon advances device 50 along the tunnel toward inferior oblique muscle 107 until stopper 36 contacts the anterior border of muscle 107. At the level of the visualized inferior oblique muscle 107, the surgeon rotates device 50 underneath muscle 107 so that transversal portion 18 of device 50 enters the portion of the tunnel just posterior to inferior oblique muscle 107. When the surgeon feels that knee 32 cannot advance any further, the surgeon slightly moves device 50 in an antero-posterior direction to allow for the accommodation of inferior oblique muscle 107 within notch 42 between transversal part 18 and stopper 36. Due to the notch 42 and the location of well 20 near distal end 58 of transversal part 18, inner core 81 is positioned directly over the portion of sclera 100 above macula 98. Proximal end 25 of longitudinal part 15 may then be sutured to sclera 100. The surgeon then closes the peritomy by suturing Tenon's capsule 101 and conjunctiva 94 to sclera 100. After closing, the surgeon places a strip of antibiotic ointment on the surgical wound. All sutures are preferably 7-0 Vicryl sutures. For the treatment of ARMD and CNV, the pharmaceutically active agent of inner core 81 is preferably one of the angiostatic steroids disclosed in U.S. Pat. Nos. 5,679,666 and 5,770,592.

The geometry of body 21 of device 50, including the concave nature of scleral surface 14; the shape and locations of transversal portion 18, well 20, opening 64, inner core 81, and retaining member 62; and the shape and locations of notch 42 and stopper 36, all facilitate the delivery of a pharmaceutically effective amount of the pharmaceutically active agent from inner core 81 through sclera 100, choroid 99, and into retina 97, and more particularly into macula 98. The absence of a polymer layer or membrane between inner core 20 and sclera 100 also greatly enhances and simplifies the delivery of an active agent to retina 97.

It is believed that device 50 can be used to deliver a pharmaceutically effective amount of a pharmaceutically active agent to retina 97 for many years, depending on the particular physicochemical properties of the pharmaceutically active agent employed. Important physicochemical properties include hydrophobicity, solubility, dissolution rate, diffusion coefficient, partitioning coefficient, and tissue affinity. After inner core 20 no longer contains active agent, the surgeon may easily remove device 50. In addition, the "pre-formed" tunnel facilitates the replacement of an old device 50 with a new device 50.

Figure 8:
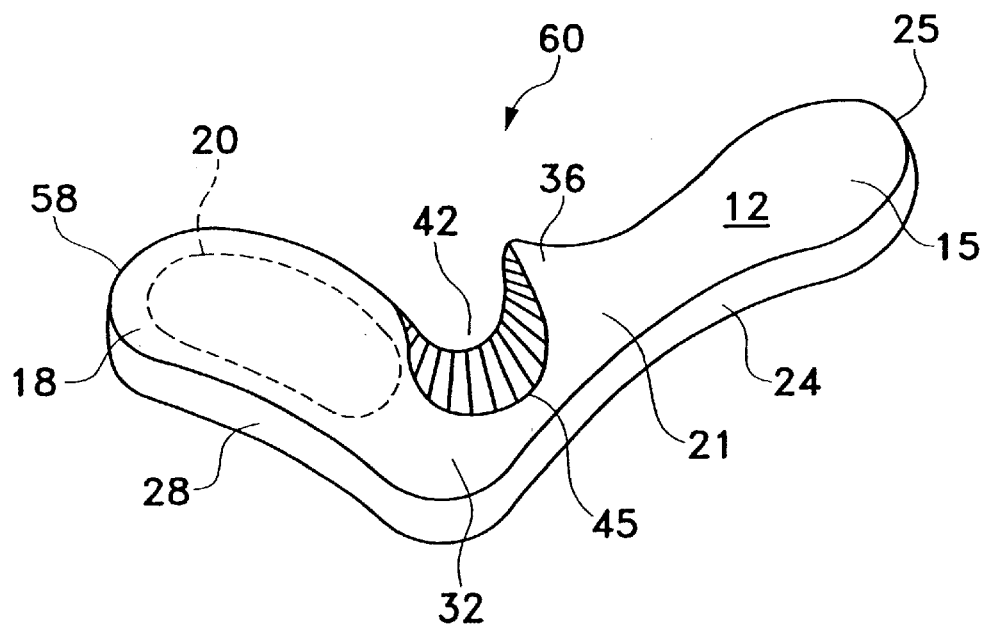
FIG. 8 is a perspective, orbital view of the ophthalmic drug delivery device of FIGS. 7 and 9 including a ramp for mating with the inferior oblique muscle.

FIG. 8 illustrates an ophthalmic drug delivery device 60, a slight modification of ophthalmic drug delivery device 50 that is useful for certain implantations of the present invention. As shown in FIG. 8, device 60 has a geometry substantially similar to device 50 of FIGS. 7 and 9, with the exception that a ramp 45 has been added to orbital surface 12 of body 21 proximate notch 42. Ramp 45 is a slanted surface that preferably travels from scleral surface 14, on a first end, to orbital surface 12 on a second end. Alternatively, ramp 45 may travel from a location within edge 24 of longitudinal part 15, on a first end, to orbital surface 12 on a second end. Ramp 45 facilitates the accommodation of inferior oblique muscle 107 within notch 42 between transversal part 18 and stopper 36 when device 60 is implanted within eye 90, as described hereinabove in connection with device 50. Device 60 may be made using techniques substantially similar to device 50.

Figure 12:
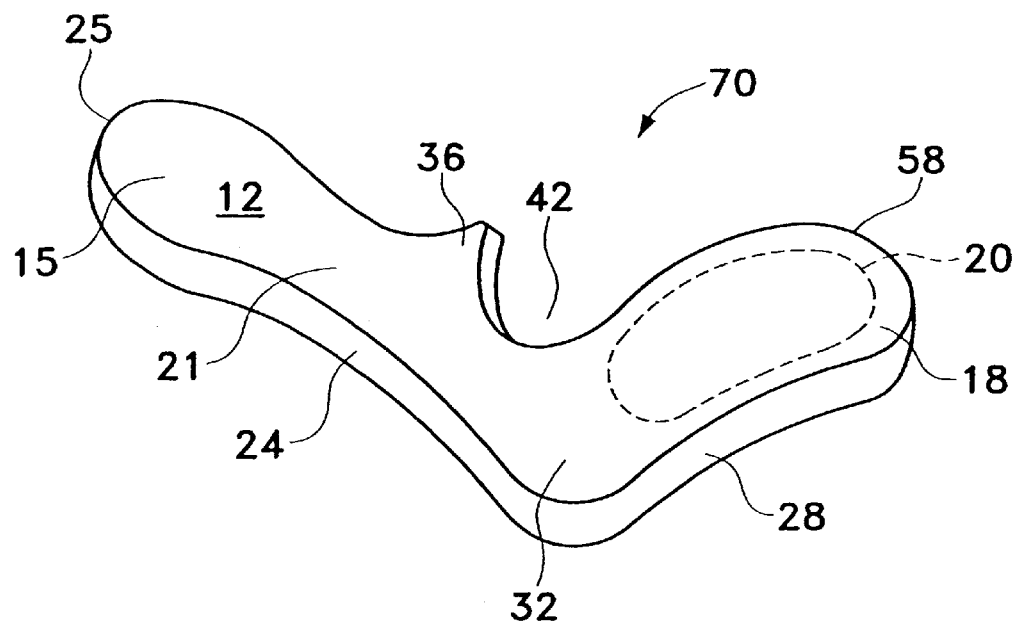
FIG. 12 is a perspective, orbital view of the ophthalmic drug delivery device of FIGS. 7 and 9 for the left human eye.
Figure 14:
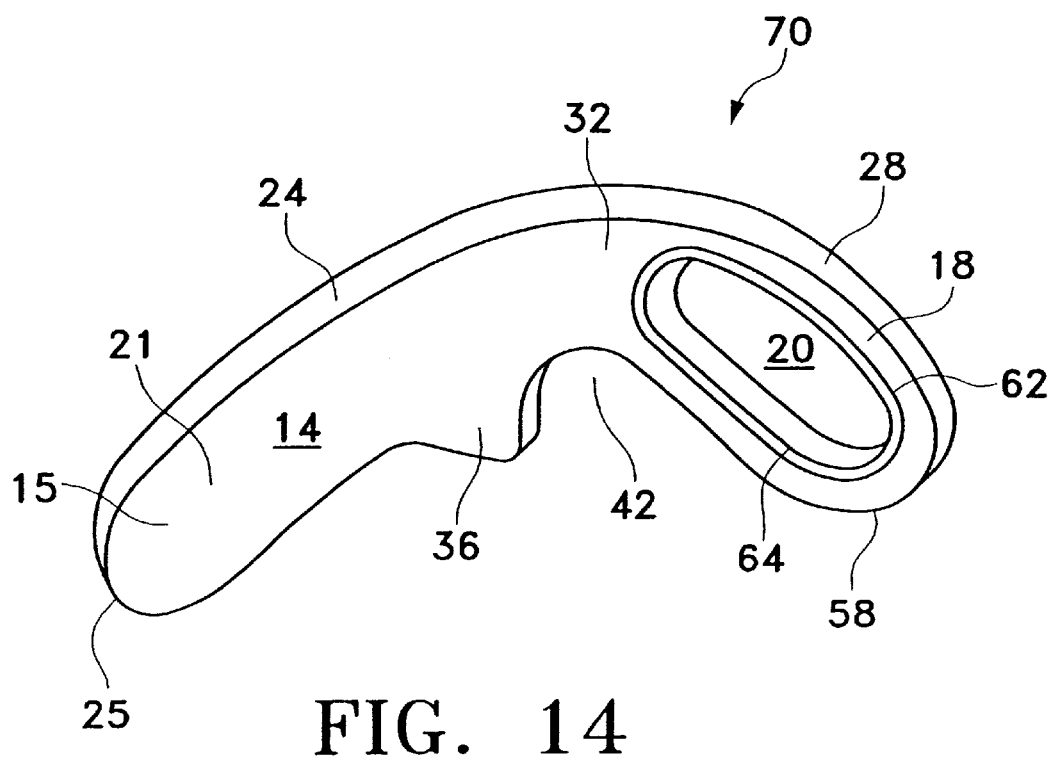
FIG. 14 is a perspective, scleral view of the ophthalmic drug delivery device of FIGS. 7 and 9 for the left human eye.

FIGS. 12 and 14 schematically illustrates an ophthalmic drug delivery device 70 for the left human eye. The geometry of device 70 is a mirror image of the geometry of device 50 for the right human eye as described hereinabove in connection with FIGS. 7 and 9. The use of device 70 is substantially identical to the use of device 50, and device 70 may be made using techniques substantially similar to device 50.

Figure 13:
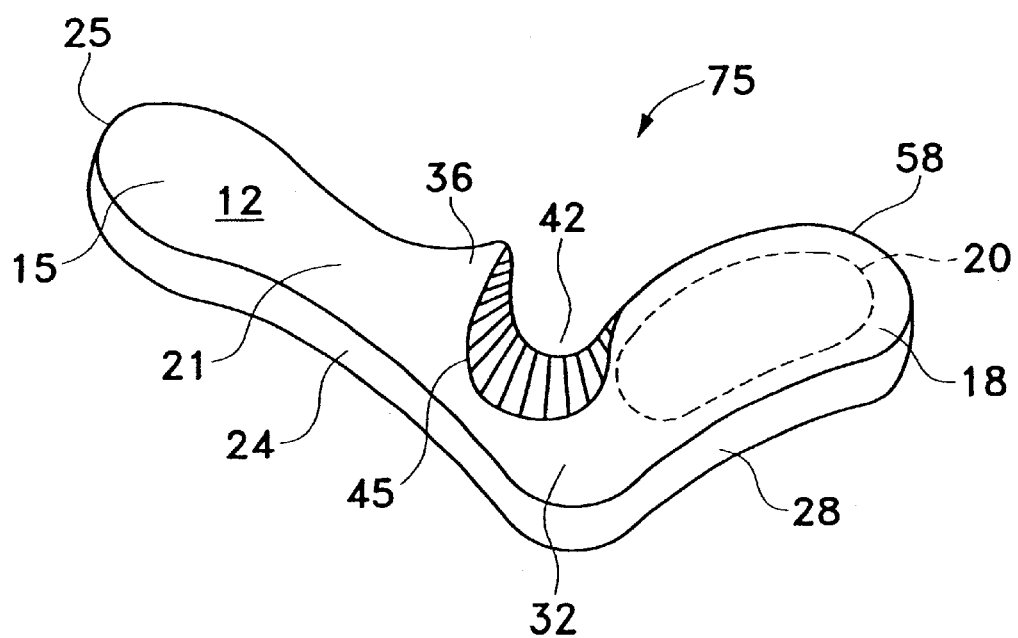
FIG. 13 is a perspective, orbital view of the ophthalmic drug delivery device of FIGS. 12 and 14 including a ramp for mating with the inferior oblique muscle.

FIG. 13 illustrates an ophthalmic drug delivery device 75 for the left human eye, a slight modification of ophthalmic drug delivery device 70 that is useful for certain implantations of the present invention. The geometry and use of device 75 of FIG. 13 is substantially similar to the geometry and use of device 60 of FIG. 8, except that device 75 is a mirror image of device 60.

Figure 15:
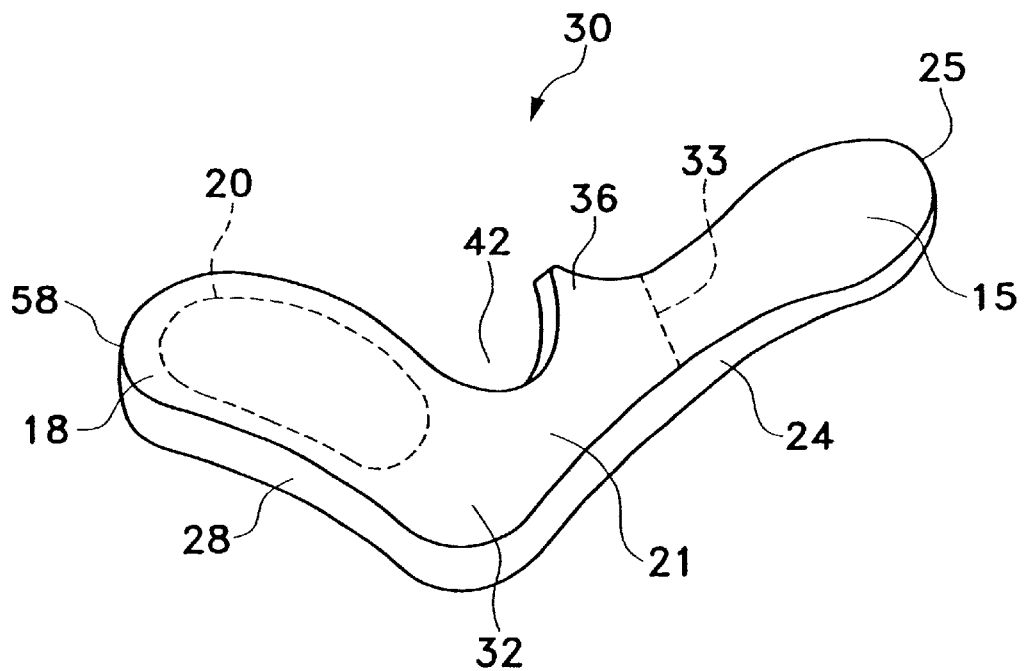
FIG. 15 is a perspective, orbital view of the ophthalmic drug delivery of FIGS. 7 and 9 including a tapered longitudinal part of the device.

FIG. 15 schematically illustrates an ophthalmic drug delivery device 30, a slight modification of ophthalmic drug delivery device 50 that is useful for certain implantations of the present invention. As shown in FIG. 15, device 30 has a geometry substantially similar to device 50 of FIGS. 7 and 9, with the exception that longitudinal part 15 has a tapered thickness, when viewed from edge 24, preferably beginning at a location 33 and continuing to proximal end 25. This portion of longitudinal part 15 is disposed anteriorly within eye 90 and may be visible to others. Therefore, due to this tapered thickness, device 30 may be more comfortable or cosmetically acceptable to the patient. The use of device 30 of FIG. 15 is substantially similar to the use of device 50, and device 30 may be made using techniques substantially similar to device 50.

Figure 16:
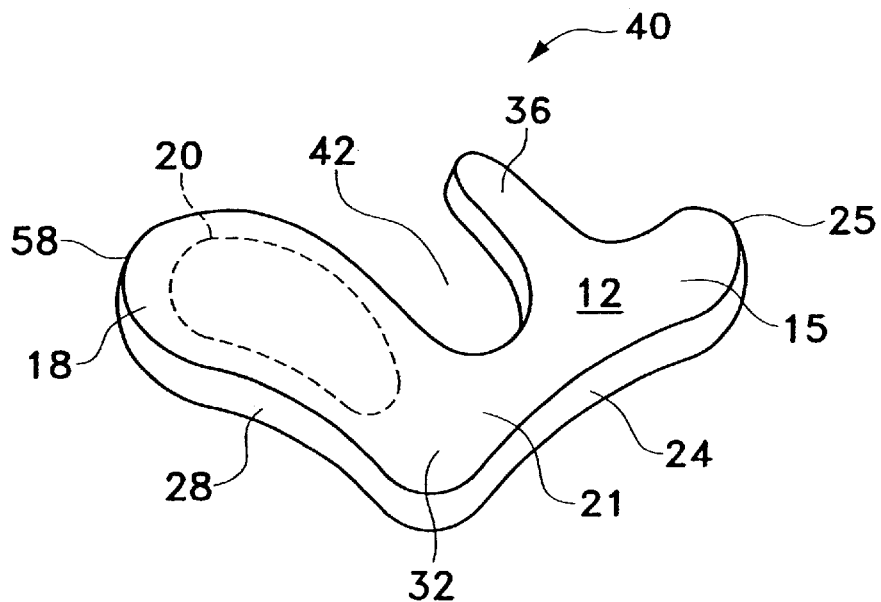
FIG. 16 is a perspective, orbital view of a shortened version of the ophthalmic drug delivery device of FIGS. 7 and 9.

FIG. 16 schematically illustrates an ophthalmic drug delivery device 40, a slight modification of ophthalmic drug delivery device 50 that is useful for certain implantations of the present invention. As shown in FIG. 16, device 40 has a geometry substantially similar to device 50 of FIGS. 7 and 9, with the exception that a length of longitudinal part 15 in device 40 has been shortened relative to device 50. Similar to device 30, this shortening of longitudinal part 15 may result in device 40 being more comfortable or cosmetically acceptable to the patient. The use of device 40 of FIG. 16 is substantially similar to the use of device 50, and device 40 may be made using techniques substantially similar to device 50.

Figure 17:
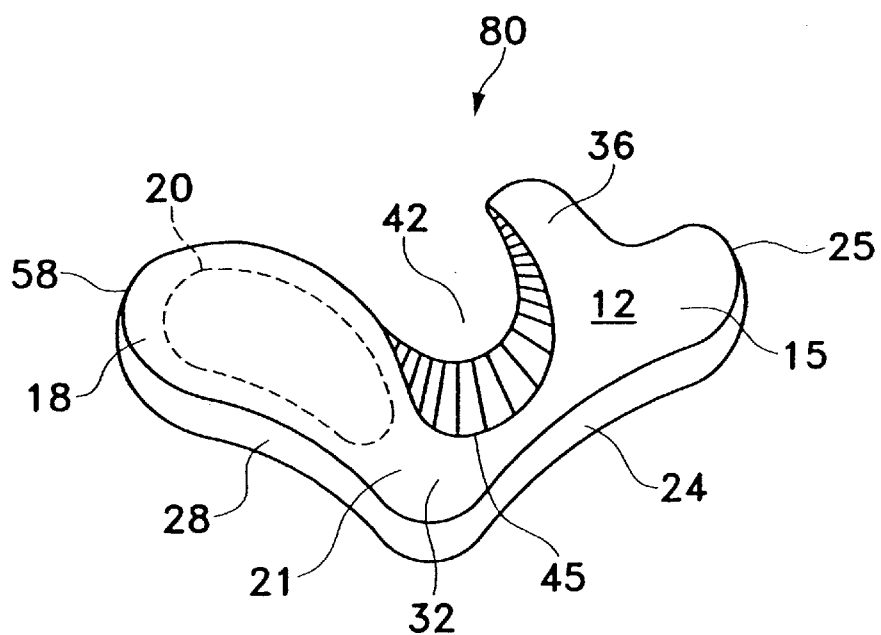
FIG. 17 is a perspective, orbital view of the ophthalmic drug delivery device of FIG. 16 including a ramp for mating with the inferior oblique muscle.

FIG. 17 illustrates an ophthalmic drug delivery device 80, a slight modification of ophthalmic drug delivery device 40 that is useful for certain implantations of the present invention. As shown in FIG. 17, device 80 has a geometry substantially similar to device 40 of FIG. 16, with the exception that a ramp 45 has been added to orbital surface 12 of body 21 proximate notch 42. Ramp 45 is a slanted surface that preferably travels from scleral surface 14, on a first end, to orbital surface 12 on a second end. Alternatively, ramp 45 may travel from a point within edge 24 of longitudinal part 15, on a first end, to orbital surface 12 on a second end. Ramp 45 facilitates the accommodation of inferior oblique muscle 107 within notch 42 between transversal part 18 and stopper 36 when device 80 is implanted within eye 90, as described hereinabove in connection with device 50. Device 80 may be made using techniques substantially similar to device 50.

Figure 18:
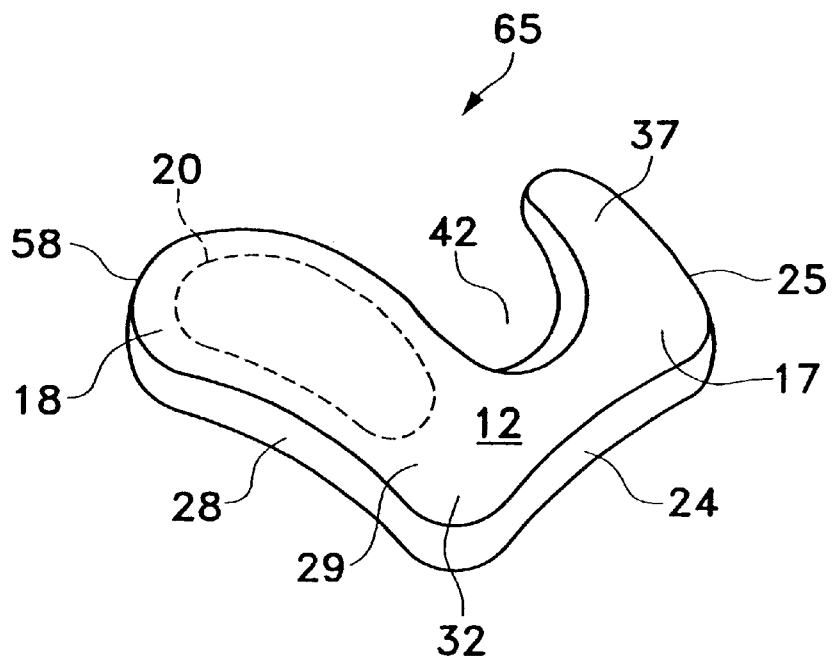
FIG. 18 is a perspective, orbital view of an ophthalmic drug delivery device for the right human eye according to a second preferred embodiment of the present invention.

FIG. 18 schematically illustrates an ophthalmic drug delivery device 65 for the right human eye according to a second preferred embodiment of the present invention. Device 65 may be used in any case where localized delivery of a pharmaceutically active agent to the eye is required. Device 65 is particularly useful for localized delivery of active agents to the posterior segment of the eye. A preferred use for device 65 is the delivery of pharmaceutically active agents to the retina proximate the macula for treating ARMD, choroidial neovascularization (CNV), retinopathies, retinitis, uveitis, macular edema, glaucoma, and neuropathies.

Device 65 generally includes a body 29 having a convex, dome-shaped, orbital surface 12 and a concave, dome-shaped, scleral surface 14 (not shown). Scleral surface 14 is designed with a radius of curvature that facilitates direct contact with sclera 100. Most preferably, scleral surface 14 is designed with a radius of curvature equal to the radius of curvature 91 of an average human eye 90. Orbital surface 12 is preferably designed with a radius of curvature that facilitates implantation under Tenon's capsule 101. When viewed from the top, body 21 preferably has a generally "C-shaped" geometry with a longitudinal part 17, a transversal part 18, and a knee 32 therebetween. Longitudinal part 17 and transversal part 18 are preferably joined at knee 32 to form an angle of about ninety degrees. Longitudinal part 17 has a proximal end 25 and a rounded edge 24. A stopper 37 forms the "lower" part of the C-shaped geometry and is preferably slightly elevated from the remainder of the generally convex orbital surface 12. A notch 42 is located in longitudinal part 17 and is defined by transversal part 18 and stopper 37. Similar to notch 42 of device 50 of FIGS. 7 and 9, notch 42 of device 65 is designed to accommodate the origin of inferior oblique muscle 107. Similar to stopper 36 of device 50, stopper 37 is designed to prevent excessive advancement of device 65 toward optic nerve 96 through contact on the anterior border of inferior oblique muscle 107. Transversal part 18 has a distal end 58, a rounded edge 28, and a well or cavity 20 having an opening 64 (not shown) to scleral surface 14 (not shown) for holding an inner core similar to those described above in connection with FIGS. 10 and 11. Well 20 and opening 64 preferably have a generally oval shape.

The use of device 65 is substantially similar to the use of device 50 as described hereinabove. Device 65 may be made using techniques substantially similar to device 50.

Figure 19:
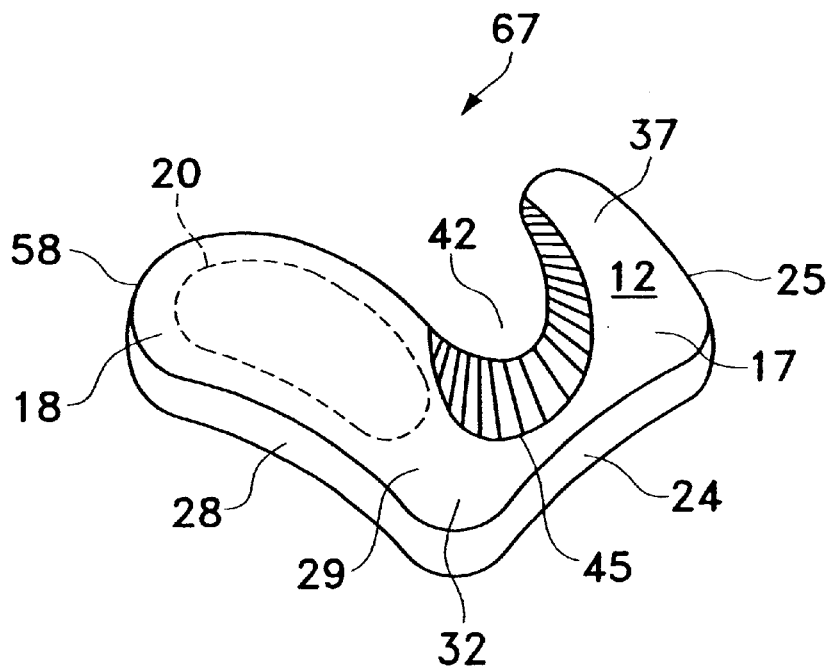
FIG. 19 is a perspective, orbital view of the ophthalmic drug delivery device of FIG. 18 including a ramp for mating with the inferior oblique muscle.

FIG. 19 illustrates an ophthalmic drug delivery device 67, a slight modification of ophthalmic drug delivery device 65 that is useful for certain implantations of the present invention. As shown in FIG. 19, device 67 has a geometry substantially similar to device 65 of FIG. 19, with the exception that a ramp 45 has been added to orbital surface 12 of body 29 proximate notch 42. Ramp 45 is a slanted surface that preferably travels from scleral surface 14, on a first end, to orbital surface 12 on a second end. Alternatively, ramp 45 may travel from a point within edge 24 of longitudinal part 17, on a first end, to orbital surface 12 on a second end. Ramp 45 facilitates the accommodation of inferior oblique muscle 107 within notch 42 between transversal part 18 and stopper 37 when device 67 is implanted within eye 90, as described hereinabove in connection with device 50. Device 67 may be made using techniques substantially similar to device 50.

Figure 20:
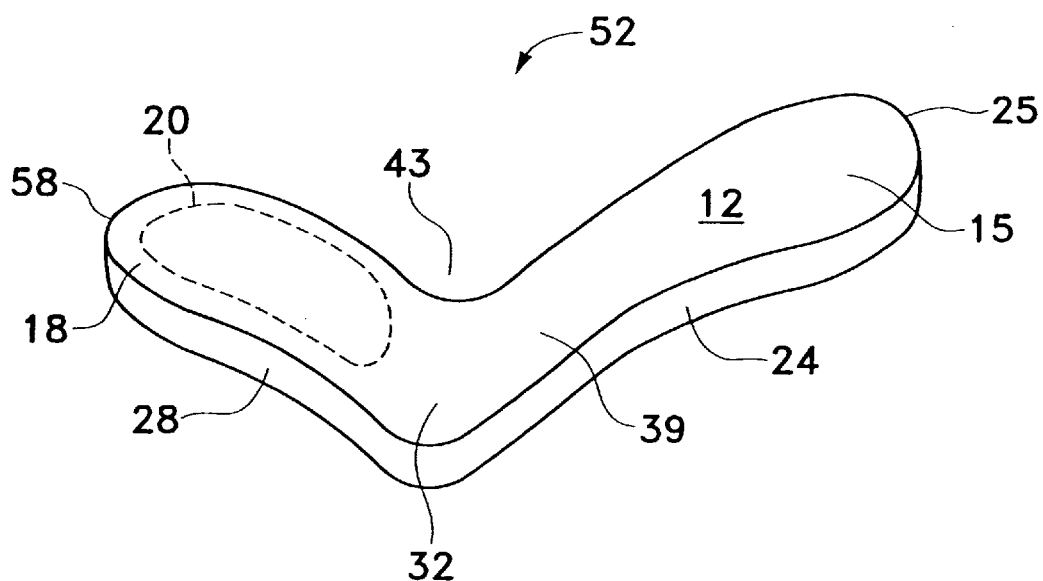
FIG. 20 is a perspective, orbital view of an ophthalmic drug delivery device for the right human eye according to a third preferred embodiment of the present invention.

FIG. 20 schematically illustrates an ophthalmic drug delivery device 52 for the right human eye according a third preferred embodiment of the present invention. Device 52 may be used in any case where localized delivery of a pharmaceutically active agent to the eye is required. Device 52 is particularly useful for localized delivery of active agents to the posterior segment of the eye. A preferred use for device 52 is the delivery of pharmaceutically active agents to the retina proximate the macula for treating ARMD, choroidial neovascularization (CNV), retinopathies, retinitis, uveitis, macular edema, glaucoma, and neuropathies.

Device 52 generally includes a body 39 having a convex, dome-shaped, orbital surface 12 and a concave, dome-shaped scleral surface 14 (not shown). Scleral surface 14 is designed with a radius of curvature that facilitates direct contact with sclera 100. Most preferably, scleral surface 14 is designed with a radius of curvature equal to the radius of curvature 91 of an average human eye 90. Orbital surface 12 is preferably designed with a radius of curvature that facilitates implantation under Tenon's capsule 101. When viewed from the top, body 39 preferably has a generally "L-shaped" geometry with a longitudinal part 15, a transversal part 18, and a knee 32 therebetween. Longitudinal part 15 and transversal part 18 are preferably joined at knee 32 to form an angle of about ninety degrees. Similar to notch 42 of device 50 of FIGS. 7 and 9, longitudinal part 15 and transversal part 18 of device 52 form a region 43 designed to accommodate the origin of inferior oblique muscle 107. Longitudinal part 15 has a proximal end 25 and a rounded edge 24. Transversal part 18 has a distal end 58, a rounded edge 28, and a well or cavity 20 having an opening 64 (not shown) to scleral surface 14 for holding an inner core similar to those described above in connection with FIGS. 10 and 11. Well 20 and opening 64 preferably have a generally oval shape.

The use of device 52 is substantially similar is substantially similar to the use of device 50 as described hereinabove. Device 52 may be made using techniques substantially similar to device 50.

Figure 21:
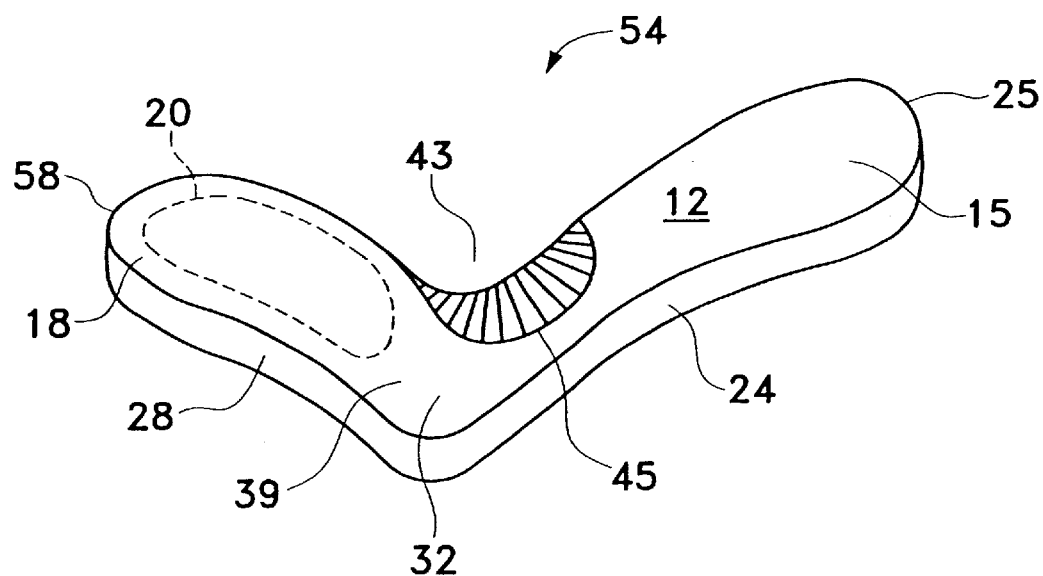
FIG. 21 is a perspective, orbital view of the ophthalmic drug delivery device of FIG. 20 including a ramp for mating with the inferior oblique muscle.

FIG. 21 illustrates an ophthalmic drug delivery device 54, a slight modification of ophthalmic drug delivery device 52 that is useful for certain implantations of the present invention. As shown in FIG. 21, device 54 has a geometry substantially similar to device 52 of FIG. 20, with the exception that a ramp 45 has been added to orbital surface 12 of body 29 proximate region 43. Ramp 45 is a slanted surface that preferably travels from scleral surface 14, on a first end, to orbital surface 12 on a second end. Alternatively, ramp 45 may travel from a point within edge 24 of longitudinal part 15, on a first end, to orbital surface 12 on a second end. Ramp 45 facilitates the accommodation of inferior oblique muscle 107 within region 43 when device 54 is implanted within eye 90, as described hereinabove in connection with device 50. Device 54 may be made using techniques substantially similar to device 50.

From the above, it may be appreciated that the present invention provides improved devices and methods for safe, effective, rate-controlled, localized delivery of a variety of pharmaceutically active agents to the eye, and particularly to the posterior segment of the eye to combat ARMD, CNV, retinopathies, retinitis, uveitis, macular edema, glaucoma, and neuropathies. The surgical procedure for implanting such devices is safe, simple, quick, and capable of being performed in an outpatient setting. Such devices are easy and economical to manufacture. Furthermore, because of their capability to deliver a wide variety of pharmaceutically active agents, such devices are useful in clinical studies to deliver various ophthalmic agents that create a specific physical condition in a patient.

The present invention is illustrated herein by example, and various modifications may be made by a person of ordinary skill in the art. For example, although the present invention is described hereinabove with reference to an ophthalmic drug delivery device having a generally "F-shaped", "C-shaped", or "L-shaped" geometry when viewed from the top, other geometries may be used, especially if they facilitate the placement of the device under the inferior oblique muscle and the location of pharmaceutically active agent over the macula when the device is implanted on the outer surface of the sclera and below the Tenon's capsule of the human eye.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A drug delivery device for a human eye, said eye having a sclera, a plurality of extraocular muscles including an inferior oblique muscle, and a macula, said device comprising:

a pharmaceutically active agent; and a body having a geometry that facilitates an implantation of said device on an outer surface of said sclera, beneath said inferior oblique muscle, with said pharmaceutically active agent disposed above said macula, and without disinsertion or cutting of any of said plurality of extraocular muscles.

2. The drug delivery device of claim 1 wherein:

said body comprises a scleral surface and an orbital surface; and said geometry is a generally F-shaped geometry when viewed from said scleral surface or said orbital surface.

3. The drug delivery device of claim 1 wherein:

said body comprises a scleral surface and an orbital surface; and said geometry is a generally C-shaped geometry when viewed from said scleral surface or said orbital surface.

4. The drug delivery device of claim 1 wherein:

said body comprises a scleral surface and an orbital surface; and said geometry is a generally L-shaped geometry when viewed from said scleral surface or said orbital surface.

5. The drug delivery device of claim 1 wherein said human eye comprises a Tenon's capsule, and said body comprises an orbital surface having a radius of curvature that facilitates said implantation of said device below said Tenon's capsule.

6. The drug delivery device of claim 5 wherein said orbital surface comprises a notch for facilitating an accommodation of said inferior oblique muscle during said implantation of said device.

7. The drug delivery device of claim 6 wherein said notch comprises a ramp.

8. The drug delivery device of claim 1 wherein said body has a scleral surface having a radius of curvature substantially equal to the radius of curvature of said human eye.

9. A method of delivering a pharmaceutically active agent to a human eye, said human eye having a sclera, a plurality of extraocular muscles including an inferior oblique muscle, and a macula, comprising the steps of:

providing a drug delivery device comprising:

a pharmaceutically active agent; and a body having a geometry that facilitates an implantation of said device on an outer surface of said sclera, beneath said inferior oblique muscle, with said pharmaceutically active agent disposed above said macula, and without disinsertion or cutting of any of said plurality of extraocular muscles; and disposing said device on said outer surface of said sclera, beneath said inferior oblique muscle, and with said pharmaceutically active agent disposed above said macula.

10. The method of claim 9 wherein:

said body comprises a scleral surface and an orbital surface; and said geometry is a generally F-shaped geometry when viewed from said scleral surface or said orbital surface.

11. The method of claim 9 wherein:

said body comprises a scleral surface and an orbital surface; and said geometry is a generally C-shaped geometry when viewed from said scleral surface or said orbital surface.

12. The method of claim 9 wherein:

said body comprises a scleral surface and an orbital surface; and said geometry is a generally L-shaped geometry when viewed from said scleral surface or said orbital surface.

* * * * *